(12) United States Patent
Notestine (10) Patent No.: US 7,288,077 B2
(45) Date of Patent: Oct. 30, 2007

(54) DEVICE AND METHOD TO ALLEVIATE LOWER BACK PAIN

(76) Inventor: Russell L. Notestine, 1660 Twin Dr., Defiance, OH (US) 43512

( * ) Notice: Subject to any disclaimer, the term of this patent is extended or adjusted under 35 U.S.C. 154(b) by 488 days.

(21) Appl. No.: 10/855,620

(22) Filed: May 28, 2004

(65) Prior Publication Data

US 2005/0277858 A1    Dec. 15, 2005

(51) Int. Cl.
A61F 5/00    (2006.01)
A61F 5/37    (2006.01)
A47C 20/00    (2006.01)
A47C 20/02    (2006.01)
A61G 15/00    (2006.01)

(52) U.S. Cl. .............. 602/19; 5/633; 5/630; 5/632; 5/652; 128/870; 128/846; 128/845; 602/5

(58) Field of Classification Search ............ 128/845, 128/846, 870; 5/630, 632, 633, 652; 482/142, 482/148
See application file for complete search history.

(56) References Cited

U.S. PATENT DOCUMENTS

| 4,230,099 A | | 10/1980 | Richardson |
| 4,299,209 A | * | 11/1981 | Behrens et al. ............... 602/19 |
| 4,840,362 A | * | 6/1989 | Bremer et al. ................ 5/632 |
| 5,007,414 A | | 4/1991 | Sexton |
| 5,224,956 A | * | 7/1993 | Dumas et al. .............. 606/240 |
| 5,774,916 A | | 7/1998 | Kurhi |

* cited by examiner

*Primary Examiner*—Patricia Bianco
*Assistant Examiner*—Tarla Patel
(74) *Attorney, Agent, or Firm*—Richard C. Litman (57) ABSTRACT

A device to alleviate lower back pain, aligning the spine in the lumbar region, stretching the spine and reducing inward curvature of the spine which is an integral, elongate, symmetrical ovoid-section rigid sheet on which the user lies in a supine position, device opening upward to receive the individual, spanning the back of the user from the buttocks to the shoulder blade area. The device, upon the user lying supine on the device, forms an air pocket formed between the user's lower spine and the surface of the device. Raising his/her knees to the chest and then lowering the feet, puts the user in a therapeutic position, the lower spine being forced down against the surface of the back due to the vacuum formed. This action applies a stretching pressure and pulls the spine down, allowing the vertebrae in the spine to align, due to the shape of the device.

4 Claims, 10 Drawing Sheets

DEVICE AND METHOD TO ALLEVIATE LOWER BACK PAIN

BACKGROUND OF THE INVENTION

1. Field of the Invention

The present invention relates to spinal adjustment devices. More particularly, the present invention relates to spinal adjustment and alignment devices against which the user lies in the supine position.

2. Description of the Related Art

The lumbar region of the back of a human often assumes positions through growth or accident which result in back pain. The spinal column may become overly curved, as well as misaligned, and slipped discs are a result of such conditions. Such a condition may be exaggerated by additional injury. Also, in females, the condition of pregnancy results in increased curvature of the spine in this region, resulting in lower back pain.

Many devices have been designed for reducing curvature or misalignment of the back, including back braces worn around the users trunk. Such braces exert pressure on the internal organs since they depend on pressure on the wearer's chest and abdomen to exert support and straightening pressure on the spinal column.

Other devices require the user to lie down on the device in a supine position, the device having an upper surface formed to cure misalignment of the spine. Such devices tend to laterally align the spine, but their effectiveness in stretching the back, i.e., reducing the inner curvature of the back is either not addressed, or is limited by the weight of the individual.

It would be desirable to provide a device that both laterally realigns the vertebrae in the spine in the lumbar region and also provides stretching or traction force to the spine, reducing the curvature of the spine in this region and thus reducing back pain thereby. It would further be desirable if such a device is capable of applying stretching and alignment pressure to the spine without the necessity of straps or the like pressing the chest and internal organs to provide desired stretching and alignment pressure.

U.S. Pat. No. 4,230,099, issued Oct. 28, 1980, to Richardson, describes a device for aligning the spine. The device is positioned beneath the back of a person lying supine on a support surface to align that person's spine. The device has two ridge members that form a convex curve that corresponds to the natural lumbar curve of a human spine.

U.S. Pat. No. 5,007,414, issued Apr. 16, 1991, to Sexton, describes a spine stretcher and aligner. This device is a spine stretcher that has two members mounted on its upper side that are composed of a compressible material that permits movement of the material toward the center of the device with the weight of the user pressed downwardly along the back on the members. This device is designed to stretch the back by increasing curvature of the spine.

U.S. Pat. No. 5,224,956, issued Jul. 6, 1993, to Dumas et al., describes a static spinal alignment device which allows the user's body weight to exert a downward force on the lumbar vertebrae to reduce lumbar lordosis while it straightens the alignment of the spine. The device of Dumas is provided in three separate parts.

U.S. Pat. No. 5,774,916, issued Jul. 7, 1998, to Kurhi, J. describes an ergonomic support member assembly contoured to a corrected spinal curvature of an individual. The device relies on body weight to realign the spine of an individual using force developed by the user's body weight.

None of the above inventions and patents, taken either singly or in combination, is seen to describe the instant invention as claimed. Thus a device to alleviate lower back pain solving the aforementioned problems is desired.

SUMMARY OF THE INVENTION

The present invention is a device to alleviate lower back pain in an individual by aligning the spine in the lumbar region, stretching the spine and reducing inward curvature of the spine. The invention is an integral, elongate, symmetrical ovoid-section rigid sheet formed of sheet plastic such as PLEXIGLAS®, a thermoplastic poly(methylmethacrylate), and a registered trademark of Rohm and Haas Co., Philadelphia, Pa. or similar material on which the user lies in a supine position, device opening upward to receive the individual. The inventive device is curved along at least one elongate axis and spans the back of the user from the buttocks to the shoulder blade area.

When the upper surface is dampened by a liquid, the device seals against the bare skin of the back of the user upon the user lying supine on the device while shirtless. An air pocket is formed between the user's lower spine and the surface of the device. Upon the user raising his/her knees to the chest, air is expelled from this air pocket forming a suction-seal to the user's lower back. The user then lowers his/her feet, the legs remaining bent at the knees, to a point near the floor. The lower spine or lumbar region of the back is held against the surface of the back due to the vacuum created by the device as a result of the above-described movement of the user, resulting in a downward force on the spine. This action applies a stretching pressure and pulls the spine down, allowing the vertebrae in the spine to align, due to the shape of the device. Adjustments to disks between the vertebrae may also adjust as a result of relieving the pressure and any misalignment of the spine.

Further downward pressure may be exerted on the spine by extending the legs outward along the floor, providing for additional downward force being exerted on the spine as it is held against the surface of the device while the hips rotate forward. This desired downward force is gained without pressure on the abdomen from torso encircling devices, up to 800 pounds of force being necessary to pull the spine straight, a force level which is unacceptable when applied against the abdomen, but achievable through use of the inventive device. The use of conventional traction devices, such as those employing the attachment of the spine to a board by nails and wire, are avoidable by the use of the present invention. The use of the device of women during and after pregnancy may relieve lower back pain often associated with that condition. Realignment and stretching of the spine by use of the inventive device may result in the realigning of internal organs into a more normal state, improving "regularity" of bowel movements and other body functions.

The device is preferably also convex-shaped in the area corresponding to the lumbar region, reaching upward slightly from floor level forming a cross-wise apex but well short of reaching the back in this area. This curvature increases the likelihood of achieving an effective seal against the body as desired. It is also desirable to make the upper, the lower and the side edges of the inventive device slightly concave in order to partially correspond with the shape of the user's back. The device is effectively used by some patients without the cross-wise curvature introduced in the shape of the inventive device, however, this added curvature increases the likelihood of achieving a good suction fit with the user's back.

It is an aspect of the invention to provide improved elements and arrangements thereof for the purposes described which is inexpensive, dependable and fully effective in accomplishing its intended purposes.

These and other aspects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The invention is a device to alleviate lower back pain in an individual and is in the form of an integral, elongate, symmetrical ovoid-section rigid sheet formed of sheet PLEXIGLAS® or similar material on which the user lies in a supine position, device opening upward to receive the individual. When upper the upper surface is dampened by a liquid, the device seals against the bare skin of the back of the user upon the user lying supine on the device. Air is expelled and a suction force between the device and the lower back is created by manipulation leg position. This force aligns, stretches, and reduced inward curvature of the spine.

Referring to FIGS. 1-4, there is shown upper perspective, inverted perspective, plan, and side elevation views, respectively, of the device to alleviate lower back pain of the present invention referred to herein by reference number 10. The device 10 is an integral, elongate, symmetrical ovoid-section rigid sheet formed of sheet PLEXIGLAS® or similar material and which is placed on a horizontal surface with the concave surface facing upward along a first elongate axis. The device has a head end edge 12 (relative to the patient), forming upper corners 13 and a lower back end edge 14 forming lower corners 15 with opposed side edges 16, respectively. The generally concave elongate device 10 forms a spinal alignment elongate apex 18 forming its centerline. The head end edge 12 and opposed side edges 16 are preferably side-cut, forming gradual concave curves to more closely conform with the back of a patient P and the upper corners 13 are preferably rounded, forming shoulder areas 20 against the shoulders of a patient P lying in the supine position on the upper surface 26 of the device 10 (shown in FIG. 3). Similarly, the lower back end edge 14 is preferably side-cut, forming a gradual concave curve to more closely fit the upper buttock area of the patient P, the lower back end edge 14 and side edges 16 forming lower corners 15 which are preferably rounded, forming upper buttock areas 22 against the upper buttocks of the patient P lying in the supine position on the upper surface 26 of the device 10.

A cross-wise lumbar apex 24 in upper surface 26 of a downward opening curved portion is formed about two-thirds of the length between the head end edge 12 and the lower back end edge 14 of the device, generally in the area of the small of the back, i.e., the lumbar region of the back of the patient P. The apex 24 is formed by a cross-wise elongate convex curve extending upward within lower surface 28 (see FIG. 2) along a second, cross-wise axis.

Figure 1:
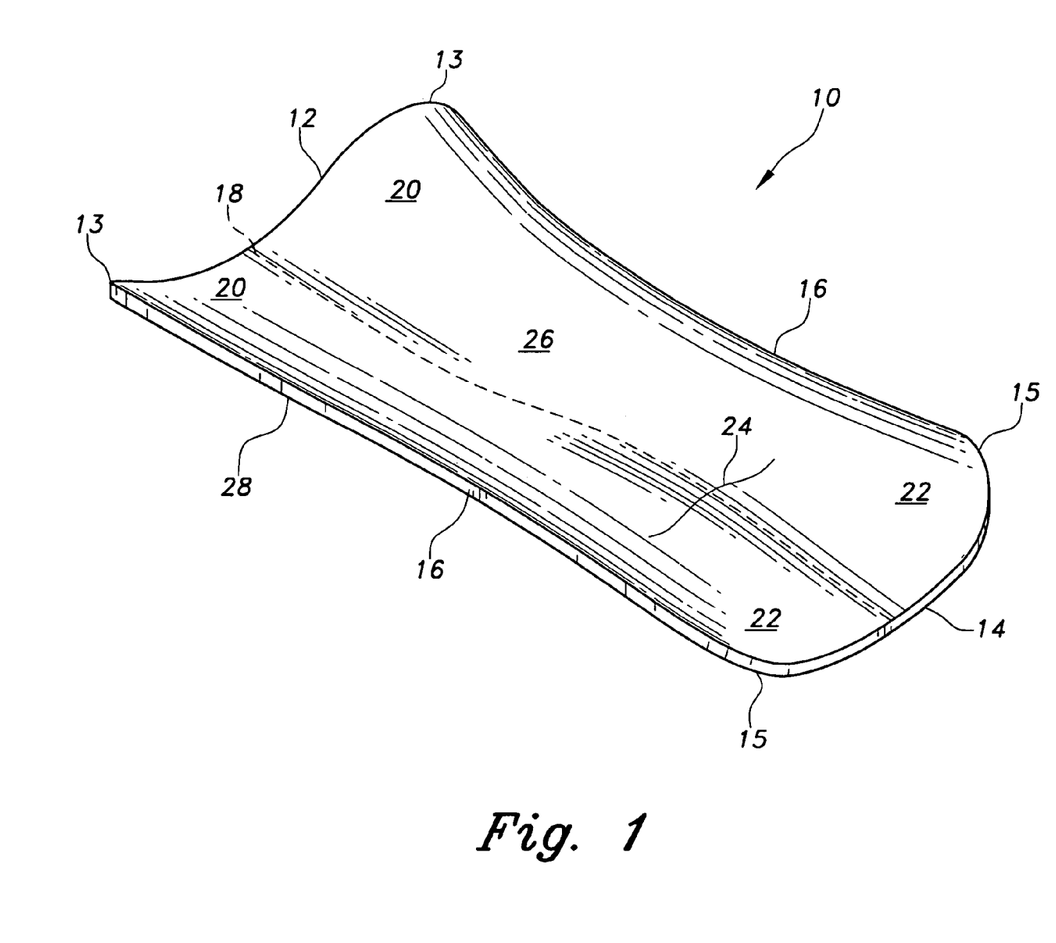
FIG. 1 is an upper, perspective view of a device to alleviate lower back pain according to the present invention.
Figure 2:
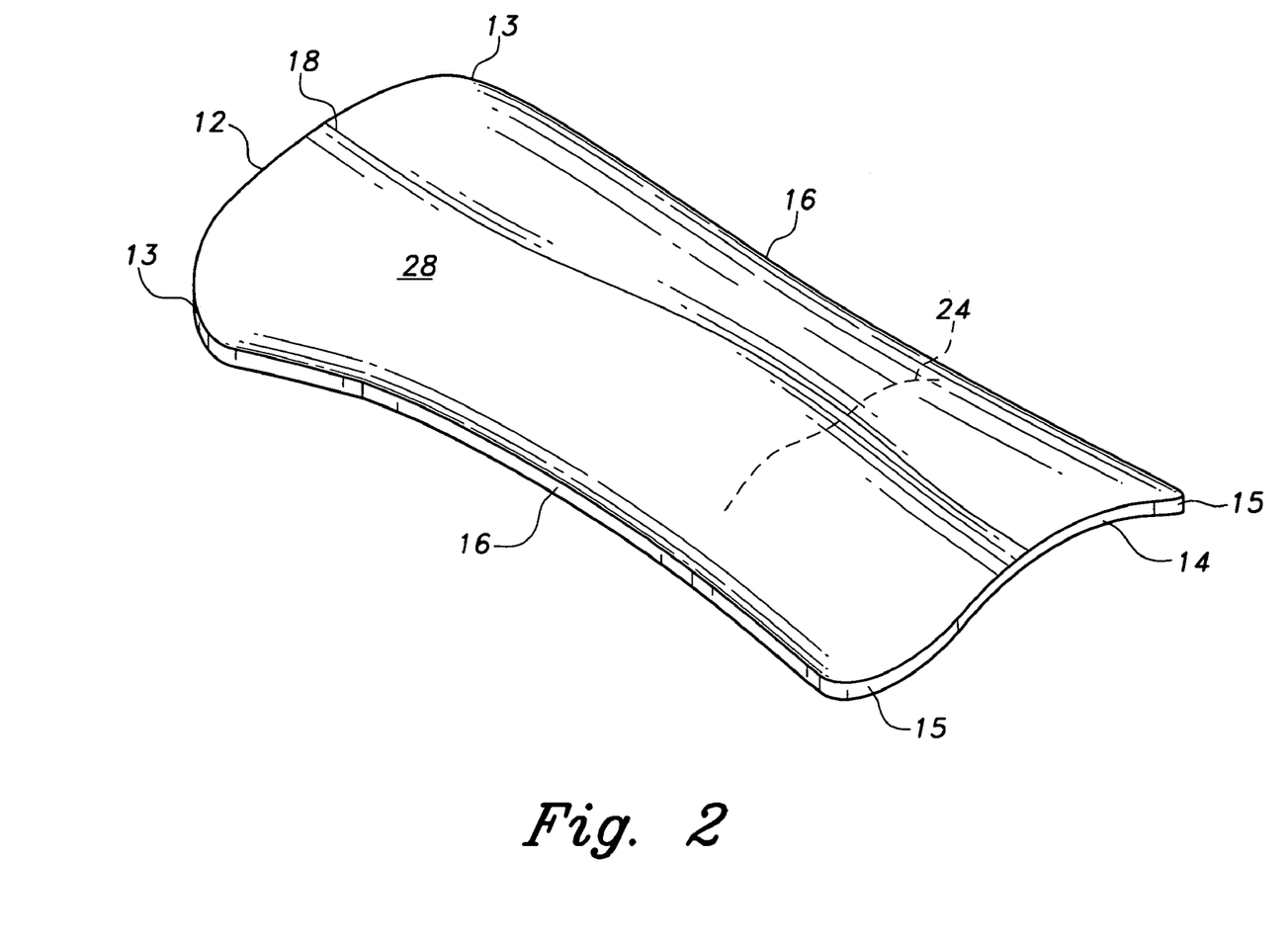
FIG. 2 is a perspective view similar to that of FIG. 1 with the device turned downward.
Figure 3:
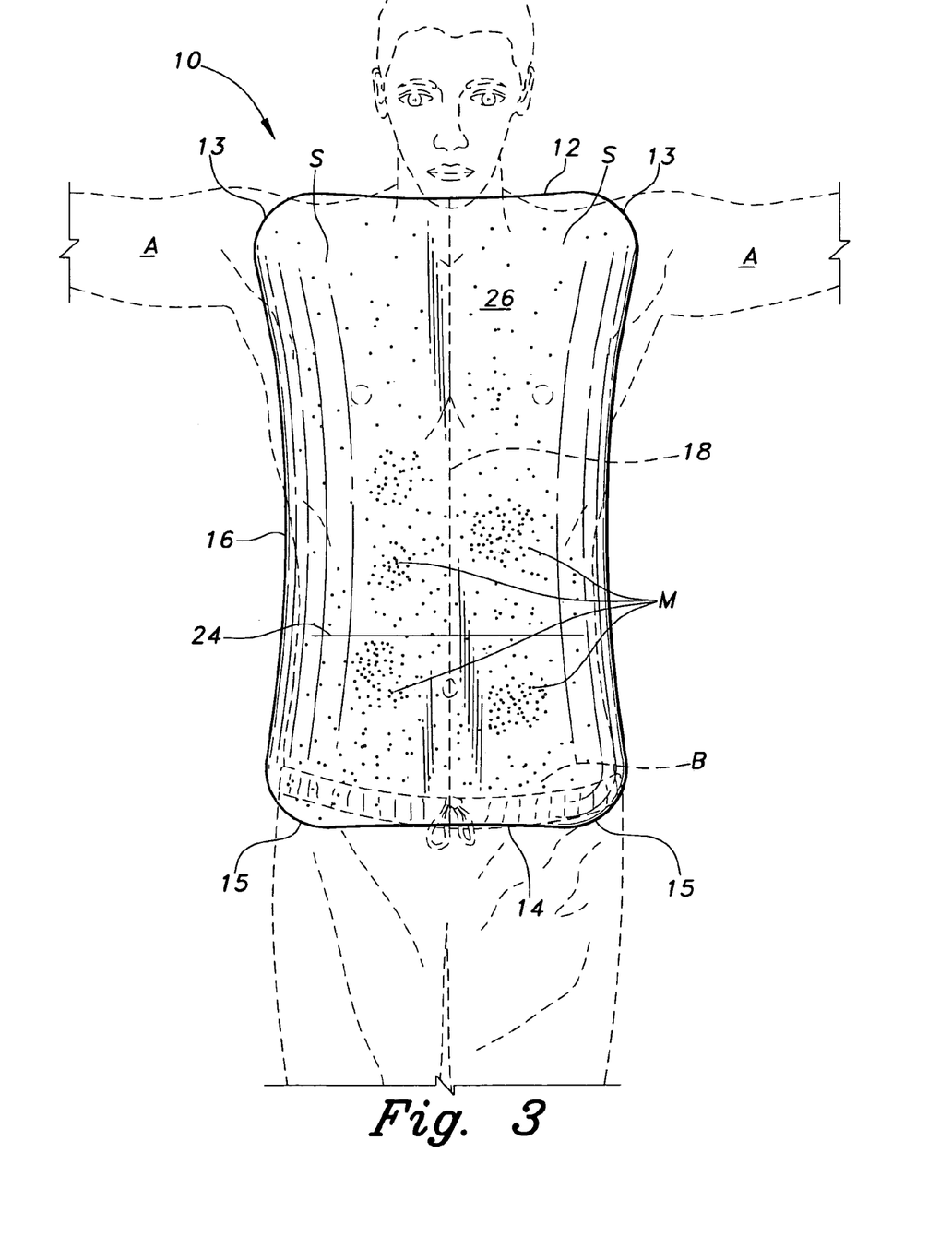
FIG. 3 is an environmental plan view of the device of FIG. 1.
Figure 4:
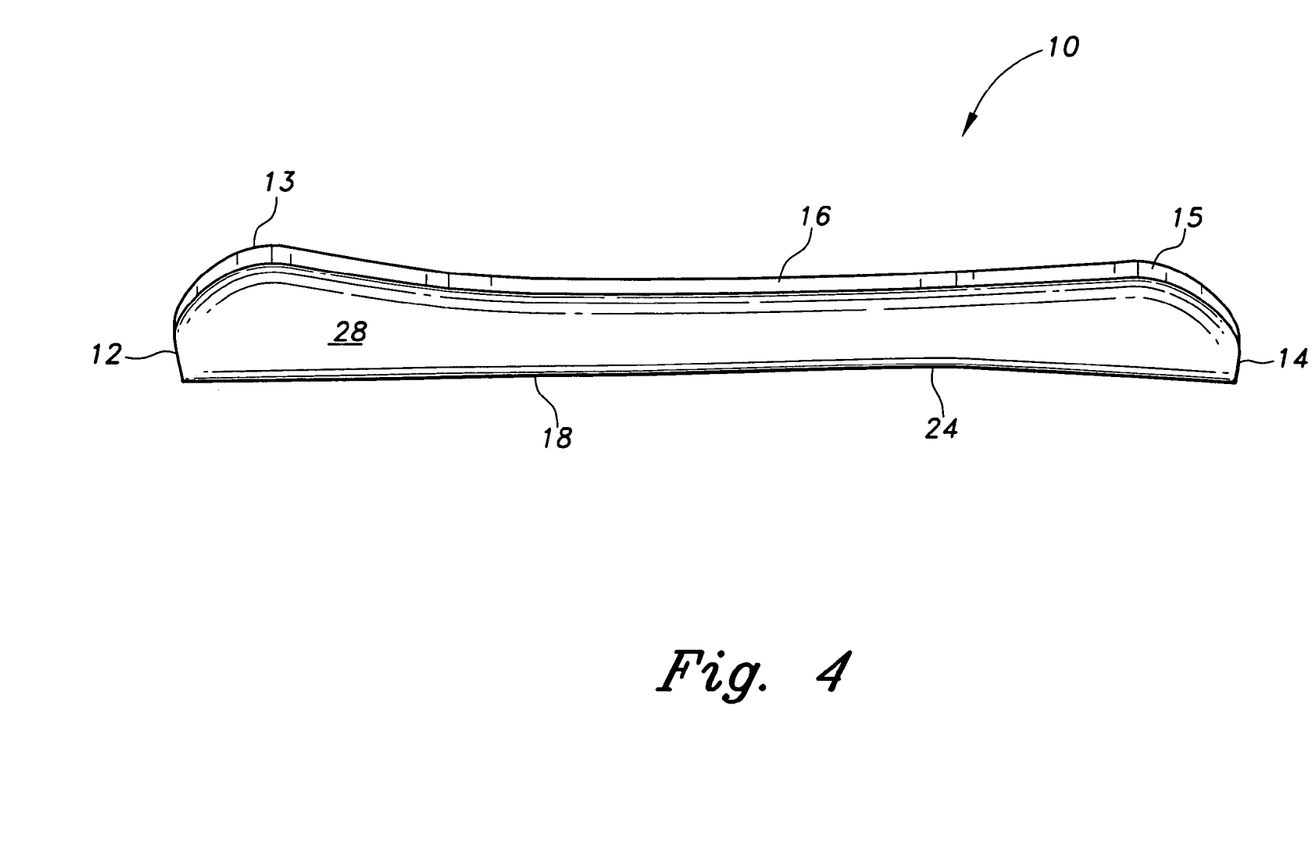
FIG. 4 is a side elevation view of the device of FIG. 1.
Figure 5A:
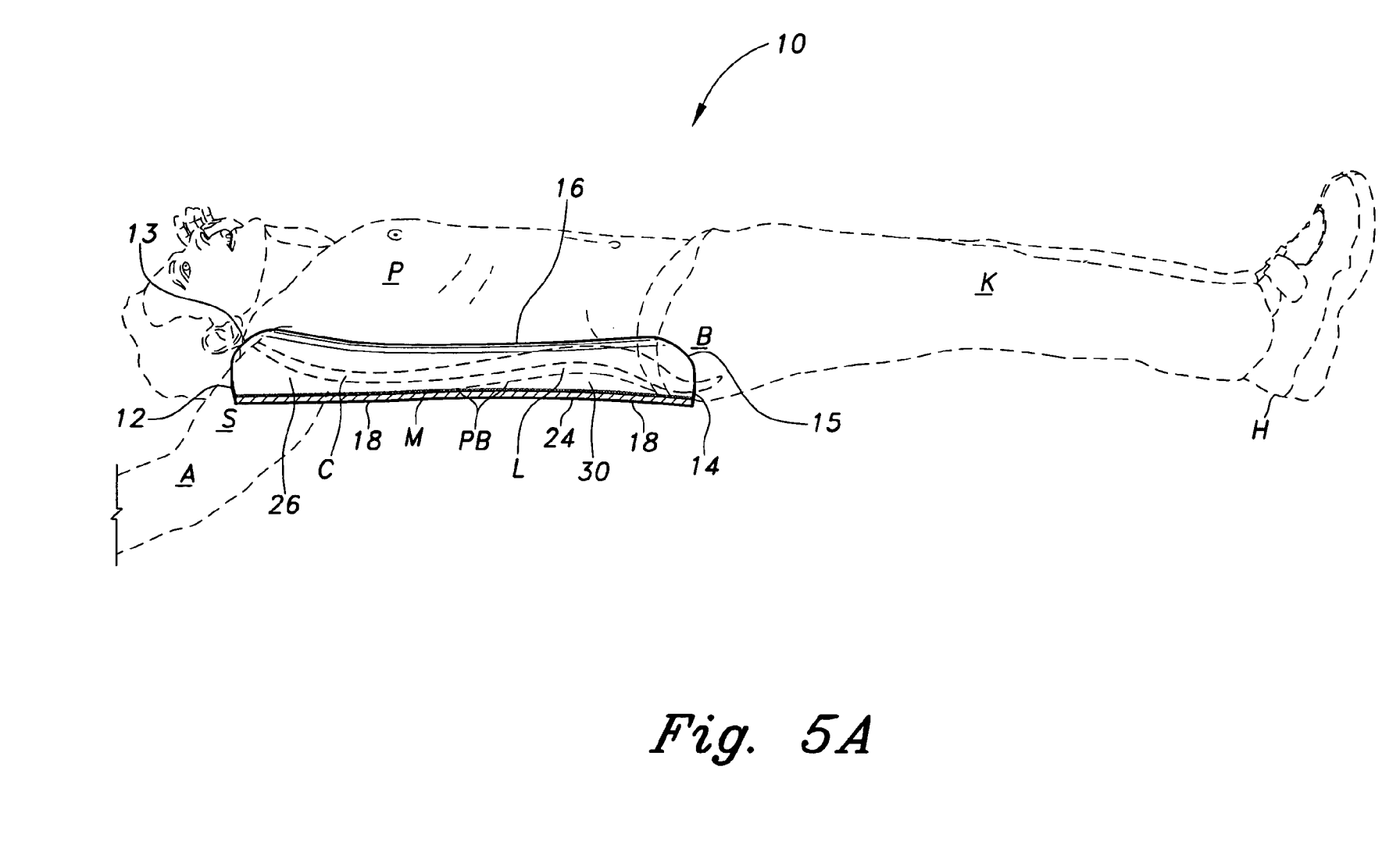
FIG. 5A is a sectional view of the device of FIG. 1 with the patient in a first position.

Referring to FIG. 5A, a patient P is shown casually lying in a supine position on the device 10 (shown in section). The patient P has arms A extending upward and outward from shoulder S resting on the shoulder area 20 (see FIG. 1). The upper surface C has been sprayed with a liquid substance such as water to form a moisture layer M on the surface against which the patient P lies. The spinal column C tends to straighten as a result of the body sinking under its own weight into the elongate cavity formed by the surface 26 of the device 10, the spinal column C conforming with spinal alignment elongate apex 18. It is noted that the lumbar section L of the spinal column C, along with the patient back PB, forms a cavity 30 relative to the upper surface 26 of the device 10. This is due to the pronounced inward curvature of the spinal column C at lumbar area L. This cavity is formed above cross-wise lumbar apex 24 which extends upward from the upper and lower end portions of spinal alignment elongate lower apex 18. This position is the first of four positions taken in sequence to utilize the device 10 for relieving back pain.

Figure 5B:
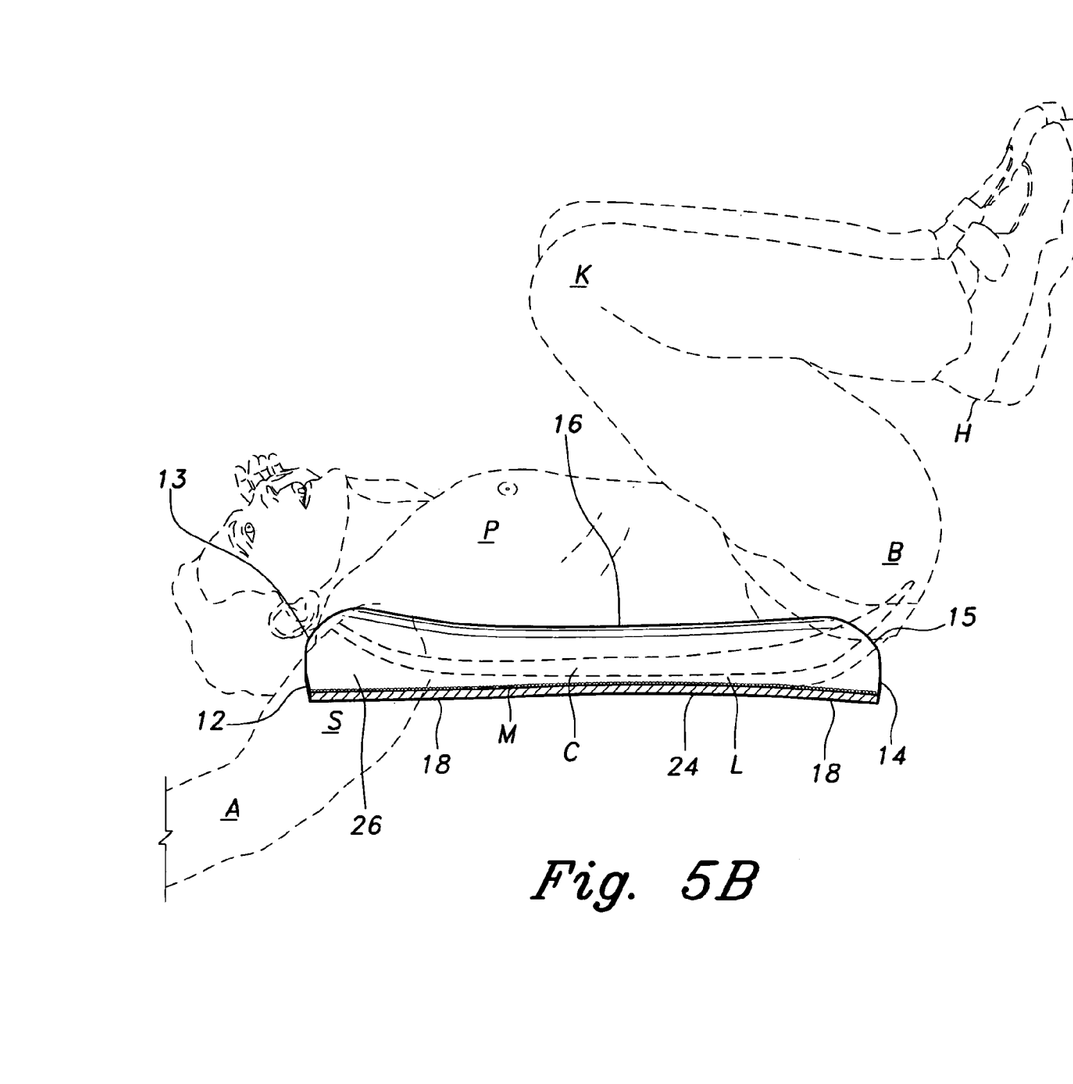
FIG. 5B is a sectional view of the device of FIG. 1 with the patient in a second position.

Referring to FIG. 5B, the patient P is shown lying in a suction forming second position with knees bent and moved upward toward his chest and his heels H held down toward his buttocks B. By assuming this position, the lumbar area of the back is forced against cross-wise lumbar apex 24 within along elongate apex 18. The air in the cavity 30 is substantially driven out, the upper surface 26 of the device forming a seal against the skin of the back of the patient P as enhanced by the presence of the moisture layer M. The lumbar portion L of the spinal column C conforms with the curvature of the upper surface 26 of the device 10.

Figure 5C:
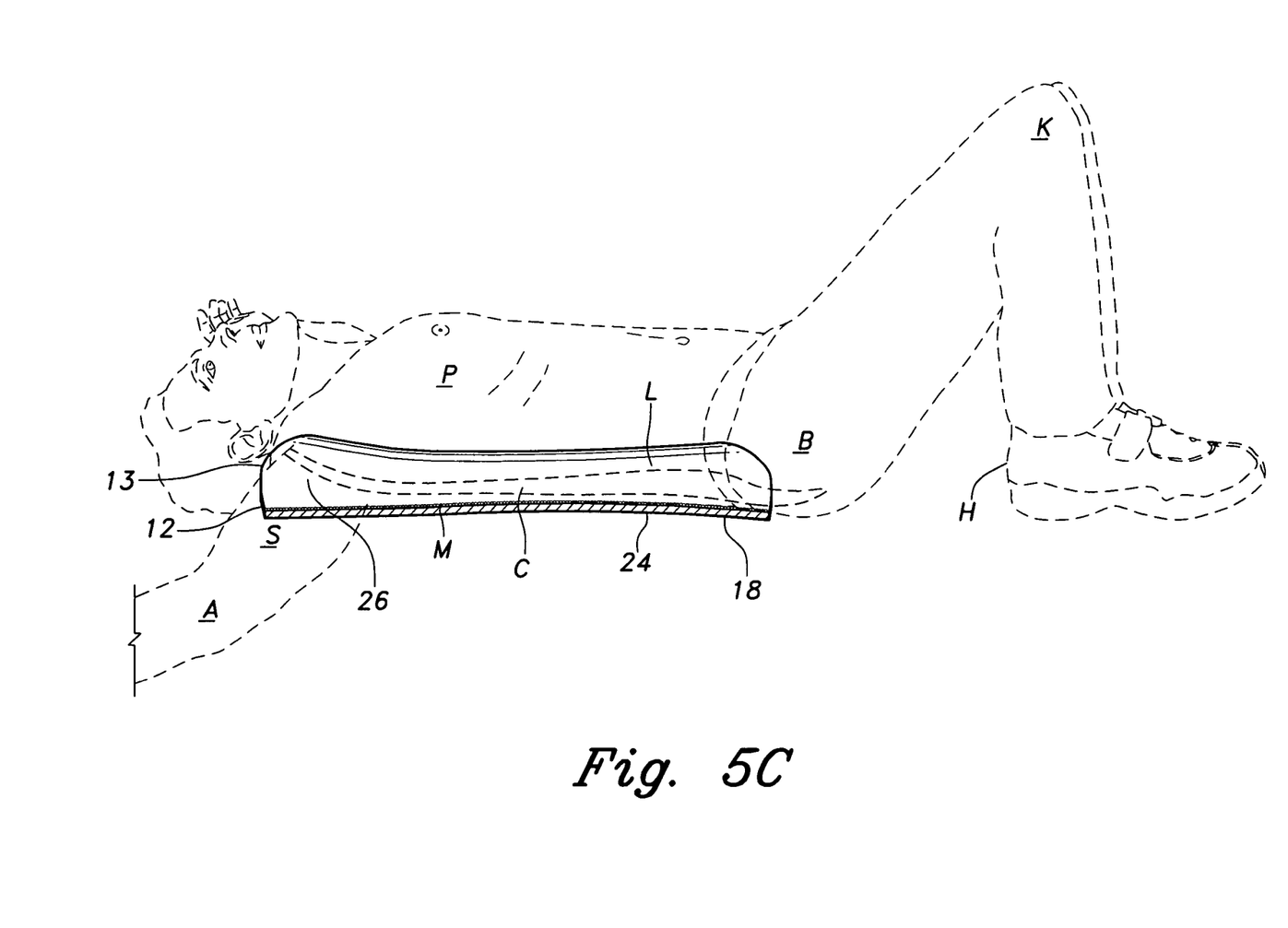
FIG. 5C is a sectional view of the device of FIG. 1 with the patient in a third suction spinal column stretching and alignment position.

Referring to FIG. 5C, the patient P is shown lying in therapeutic third position with heels H lowered to a point near the level of the device 10 with knees K still bent. It is noted the buttocks B rotate forward between positions 2 and 3 and this movement would ordinarily allow the lumbar region L to lift away from the upper surface of the device 10 in the area of the cross-wise lumbar apex 24 to form the cavity 30 (see FIG. 5A). However, the interaction of the lower back of patient P with the upper surface of device 10 having moisture layer M thereon maintains suction on the lumbar region L, maintaining it in the same relative position to the upper surface of device 10 in the vicinity of the cross-wise lumbar apex 24 as in the second position. This results in downward suction force (due to atmospheric pressure) being applied to the lumbar region L of the patients back, resulting in the stretching and reduction of inward curvature of the back relative to the buttocks and attendant relief of lower pack pain.

Figure 5D:
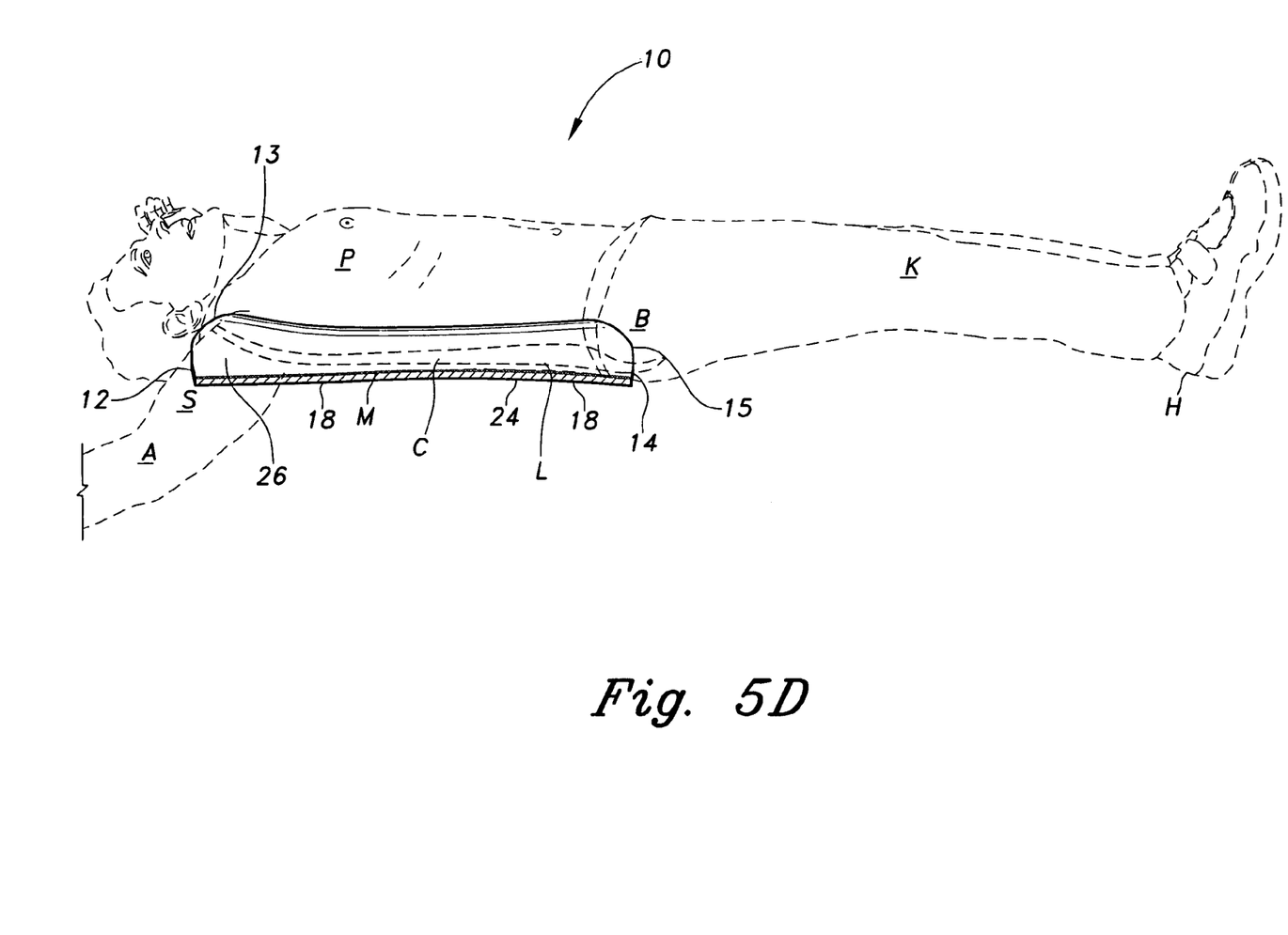
FIG. 5D is a sectional view of the device of FIG. 1 with the patient in a fourth suction spinal column stretching and alignment position.

Referring to FIG. 5D, the patient P is shown lying in a therapeutic fourth position wherein the heels H have been extended forward from the third position and the knees held straight. Assuming this position rotates the hips and buttocks B further forward, resulting in more lumbar straightening pressure on the lumbar region relative to the hips and buttocks, maximizing the therapeutic effect of the lower back pain relief device 10 of the present invention.

Figure 6A:
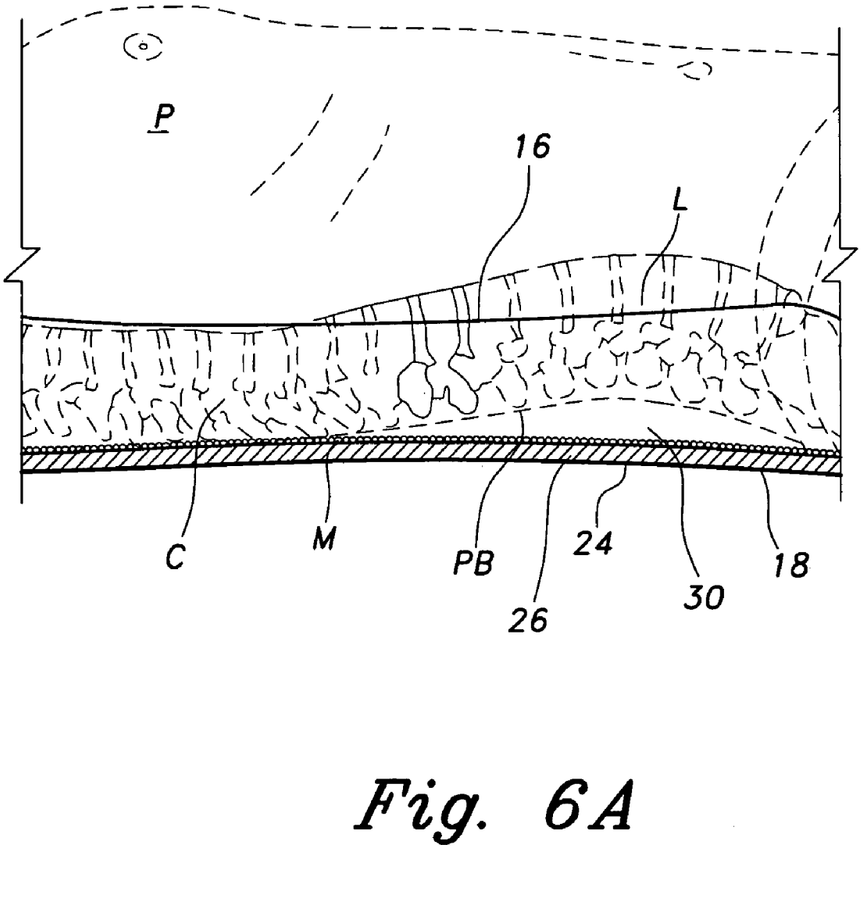
FIG. 6A is detail view of FIG. 5A showing the lumbar region of the spinal column.
Figure 6B:
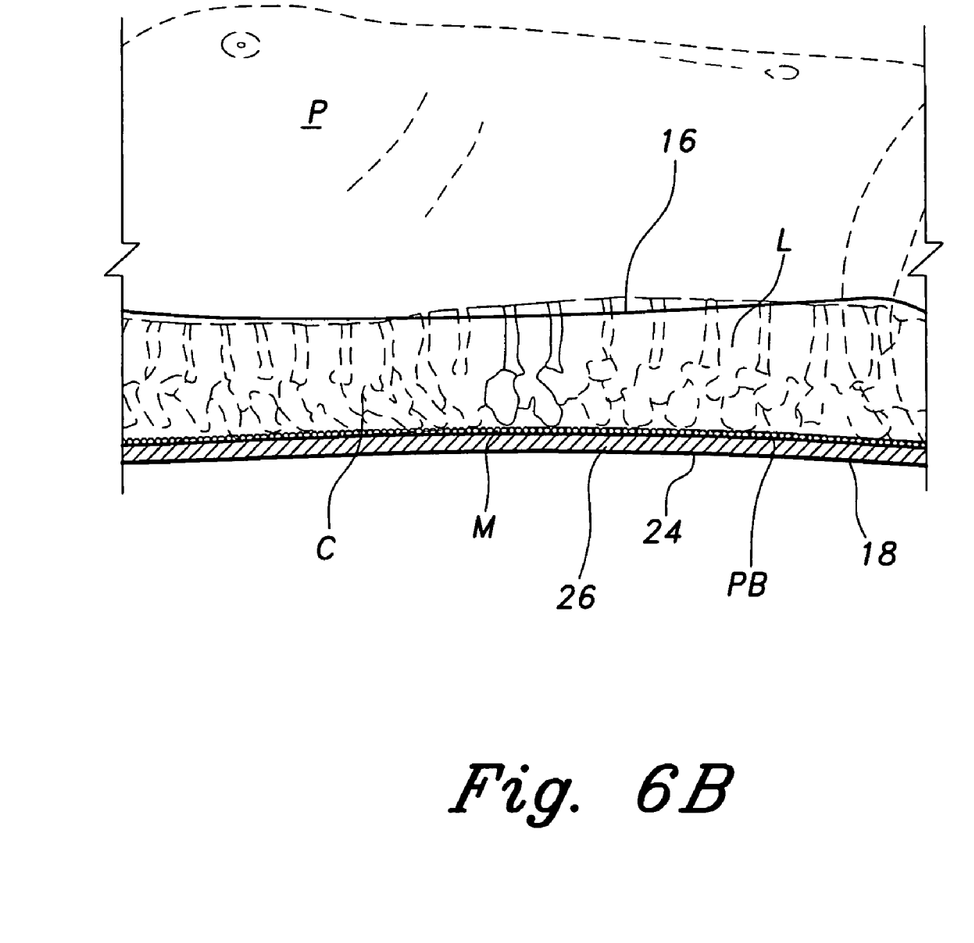
FIG. 6B is a detail view of FIG. 5D showing the lumbar region of the spinal column held under suction force in an aligned, stretched position.

Referring to FIGS. 6A and 6B, there are shown detail views of the lumbar area L as in FIGS. 5A and 5D. In FIG. 6A, the spinal column C of the patient P is decidedly curved, forming air cavity 30 between the patient's lower back and the upper surface of the device 10 in the vicinity of the cross-wise lumbar apex 24 when the patient is lying in a casual position. It is also noted that the spinal column C aligns with the apex 18 of the device. In FIG. 6B, the spinal column C in the lumbar region is shown under suction pressure with the patient lying in a therapeutic position as the legs are extended as in FIGS. 5C and 5D with the lumbar region L held downward against the upper surface of the device 10 in the general area of the cross-wise lumbar apex 24 and moisture layer M. It is noted that when held in this position, the lumbar region L of spinal column C is also centered and straightened along elongate apex 18 by the weight of the patient against the curvature of the upper surface of the device 10.

The repositioning of vertebrae of the patient during the use and practice of the present invention in the therapeutic supine position as described above allows muscles in the lower back to relax through the removal of stresses therefrom. The preferred dimensions of the device as used by adults is about 24" in length by about 18" in width, the dimensions being subject to variation to fit a particular person or child. The inventive device is preferably made of PLEXIGLAS® of 1/8" or more in thickness, the thermoplastic material being formed into the desired shape by heating over a mold. The "springiness" of the material as well as its limited flexibility increases the likelihood of obtaining a good seal against the back, however, a solid piece of material may be carved to present an upward surface like that of the present invention as shown as desired to accomplish similar results. The primary use of the present invention is to align, straighten, stretch, and readjust the lumbar region of the lower back, although the device is helpful in aligning the upper back, also. The use of the present invention may be particularly useful in helping women recover from childbirth. Some digestive tract problems may be alleviated by realigning internal organs as a benefit of aligning the back employing the present invention. The "regularity" of a person, for example, may be improved by removing kinks in the small or large intestine.

It is to be understood that the present invention is not limited to the embodiment described above, but encompasses any and all embodiments within the scope of the following claims.

I claim:

1. A method for alleviating lower back pain in a patient comprising the steps of:

providing a device to alleviate lower back pain in a patient lying in a supine position with his/her back thereon, said device consisting essentially of a patient support rigid element having an imperforate, integral, elongate, symmetrical ovoid-section shaped upper surface defining an elongate axis and an elongate centrally located apex, said ovoid section being concave and opening upward from said elongate apex, said rigid element upper surface having a length extending from about the shoulder to the upper buttocks region of said patient and a width corresponding to the width of the back of the patient, said support element having opposed sidewall edges, a head end edge and a lower back end edge defining, respectively, the upper and lower boundaries of the support element between the opposed sidewall edges, said head end edge, said lower back end edge and said sidewall edges each being side-cut, forming shallow concave curves therein, said head end edge and said sidewall edges forming rounded corners defining patient shoulder areas of said upper surface, said lower back end edge and said sidewalls forming rounded corners defining patient upper buttock areas;

applying liquid to the upper surface of said device, forming a moisture layer thereon;

the patient casually lying in a supine position on said device between his/her shoulders and upper buttocks;

the patient lifting his/her knees to their chest, thereby pushing air from the air pocket defined by said surface and the lumbar portion of the patient's back; and the patient lowering his/her knees and rotating their hips and buttocks such that the heels of their feet are on or near the level of said device to form a therapeutic position with suction force forcing the lower back and lumbar region against said device upper surface.

2. The method of claim 1, further comprising the step of the patient extending his/her heels outward at or near the level of said device while straightening their knees and further rotating their hips and buttocks to form a further therapeutic position with greater suction force forcing the lower back and lumbar region against said device upper surface.

3. A method for alleviating lower back pain in a patient comprising the steps of:

providing a device to alleviate lower back pain in a patient lying in a supine position with his/her back thereon, said device consisting essentially of a patient support rigid element having an imperforate, integral, elongate, symmetrical ovoid-section shaped upper surface defining an elongate axis and an elongate centrally located apex, said ovoid section being concave and opening upward from said elongate apex, said rigid element upper surface having a length extending from about the shoulder to the upper buttocks region of said patient and a width corresponding to the width of the back of the patient, said support element having opposed sidewall edges, a head end edge and a lower back end edge defining, respectively, the upper and lower boundaries of the support element between the opposed sidewall edges, said surface being further defined by a cross-wise convex curved surface spaced about two-thirds of the length from the shoulder to the buttocks region of the patient and corresponding to the lumbar region thereof, said cross-wise convex curved surface forming a cross-wise apex relative to said elongate apex, said convex curved surface and the small or lumbar region of the patient's back defining an air cavity when said patient is casually lying in a supine position, wherein the small or lumbar region of said patient's back conforms with said cross-wise convex curved surface within said elongate concave surface when said patient is lying in a therapeutic position as a result of suction force therebetween;

applying liquid to the upper surface of said device, forming a moisture layer thereon;

the patient casually lying in a supine position on said device between his/her shoulders and upper buttocks;

the patient lifting his/her knees to their chest, thereby pushing air from the air pocket defined by said surface and the lumbar portion of the patient's back; and the patient lowering his/her knees and rotating their hips and buttocks such that the heels of their feet are on or near the level of said device to form a therapeutic position with suction force forcing the lower back and lumbar region against said device upper surface.

4. The method of claim 3, further comprising the step of the patient extending his/her heels outward at or near the level of said device while straightening their knees and further rotating their hips and buttocks to form a further therapeutic position with greater suction force forcing the lower back and lumbar region against said device upper surface.

* * * * *